(12) United States Patent
Wang et al.

(10) Patent No.: US 8,588,496 B2
(45) Date of Patent: Nov. 19, 2013

(54) MEDICAL IMAGE DISPLAY APPARATUS, MEDICAL IMAGE DISPLAY METHOD AND PROGRAM

(75) Inventors: Caihua Wang, Tokyo (JP); Yoshiyuki Moriya, Tokyo (JP)

(73) Assignee: Fujifilm Corporation, Tokyo (JP)

( * ) Notice: Subject to any disclaimer, the term of this patent is extended or adjusted under 35 U.S.C. 154(b) by 423 days.

(21) Appl. No.: 12/979,951

(22) Filed: Dec. 28, 2010

(65) Prior Publication Data

US 2011/0194744 A1    Aug. 11, 2011

(30) Foreign Application Priority Data

Feb. 5, 2010   (JP) ................................. 2010-024587

(51) Int. Cl.
*G06K 9/00*   (2006.01)

(52) U.S. Cl.
USPC ........................................................ 382/131

(58) Field of Classification Search
None
See application file for complete search history.

(56) References Cited

U.S. PATENT DOCUMENTS

| | | | | |
|---|---|---|---|---|
| 5,412,563 | A * | 5/1995 | Cline et al. ..................... | 345/420 |
| 6,049,622 | A * | 4/2000 | Robb et al. ..................... | 382/128 |
| 7,736,316 | B2 | 6/2010 | Kawashima et al. | |
| 2007/0078343 | A1 | 4/2007 | Kawashima et al. | |
| 2008/0298653 | A1 | 12/2008 | Amunts et al. | |
| 2009/0087058 | A1 | 4/2009 | Ihara | |
| 2009/0245609 | A1 | 10/2009 | Sakaida et al. | |
| 2010/0231605 | A1 | 9/2010 | Moriya et al. | |
| 2013/0018497 | A1 * | 1/2013 | Dean et al. ...................... | 700/98 |

FOREIGN PATENT DOCUMENTS

| | | |
|---|---|---|
| JP | 01-140377 | 6/1989 |
| JP | 2002-263101 | 9/2002 |
| JP | 2003-199715 | 7/2003 |
| JP | 2005-312770 | 11/2005 |
| JP | 2008-043524 | 2/2008 |
| JP | 2008-073397 | 4/2008 |
| JP | 2009-082463 | 4/2009 |
| JP | 2009-518060 | 5/2009 |

* cited by examiner

*Primary Examiner* — Claire X Wang
(74) *Attorney, Agent, or Firm* — Young & Thompson

(57) ABSTRACT

A medical image display apparatus includes an image database for recording a three-dimensional standard image of a model subject, a three-dimensional anatomical image corresponding to the three-dimensional standard image, and anatomical information on living tissue names, an image acquirer for acquiring a three-dimensional medical image of an examinee, a medical tomographic image identifier for identifying a medical tomographic image in the three-dimensional medical image based on a user's instruction, a standard tomographic image identifier for identifying a standard tomographic image in the three-dimensional standard image, which corresponds to the medical tomographic image, an anatomical tomographic image identifier for identifying an anatomical tomographic image in the three-dimensional anatomical image, which corresponds to the standard tomographic image, and a display controller for displaying the medical tomographic image and the anatomical tomographic image on a display unit, while displaying the living tissue names over the anatomical tomographic image based on the anatomical information.

6 Claims, 10 Drawing Sheets

FIG. 5

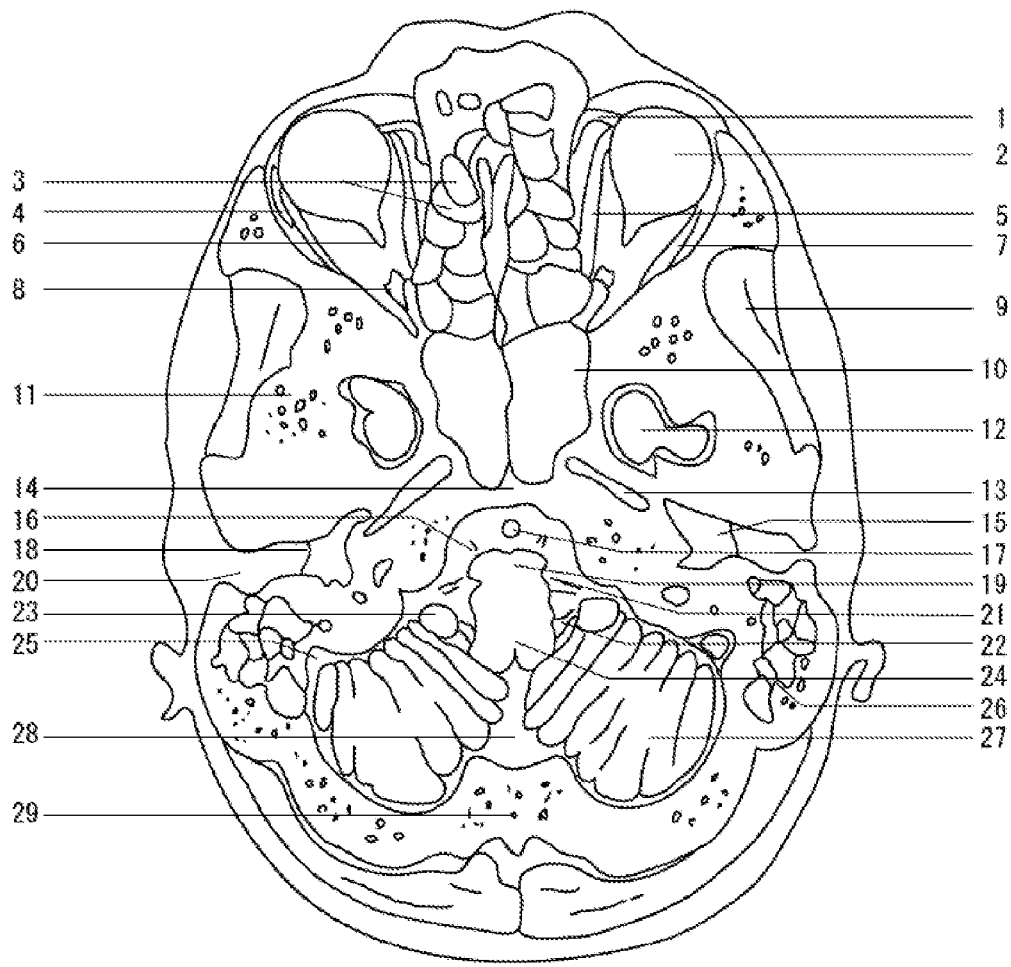

1 superior oblique muscle
2 eyeball
3 ethmoid labyrinth
4 lacrimal gland
5 medial rectus muscle
6 optic nerve
7 lateral rectus muscle
8 superior rectus muscle
9 temporalis muscle
10 sphenoid sinus
11 temporal bone
12 temporal lobe (base)
13 internal carotid artery
14 clivus
15 tympanic cavity
16 abducens nerve
17 basilar artery
18 tympanic membrane
19 pons
20 external auditory canal
21 anterior inferior cerebellar artery
22 glossopharyngeal and vagus nerves
23 floccule
24 medulla oblongata
25 sigmoid sinus
26 mastoid air cells
27 cerebellar hemisphere (caudal lobe)
28 cisterna magna
   (cerebellomedullary cistern)
29 occipital bone

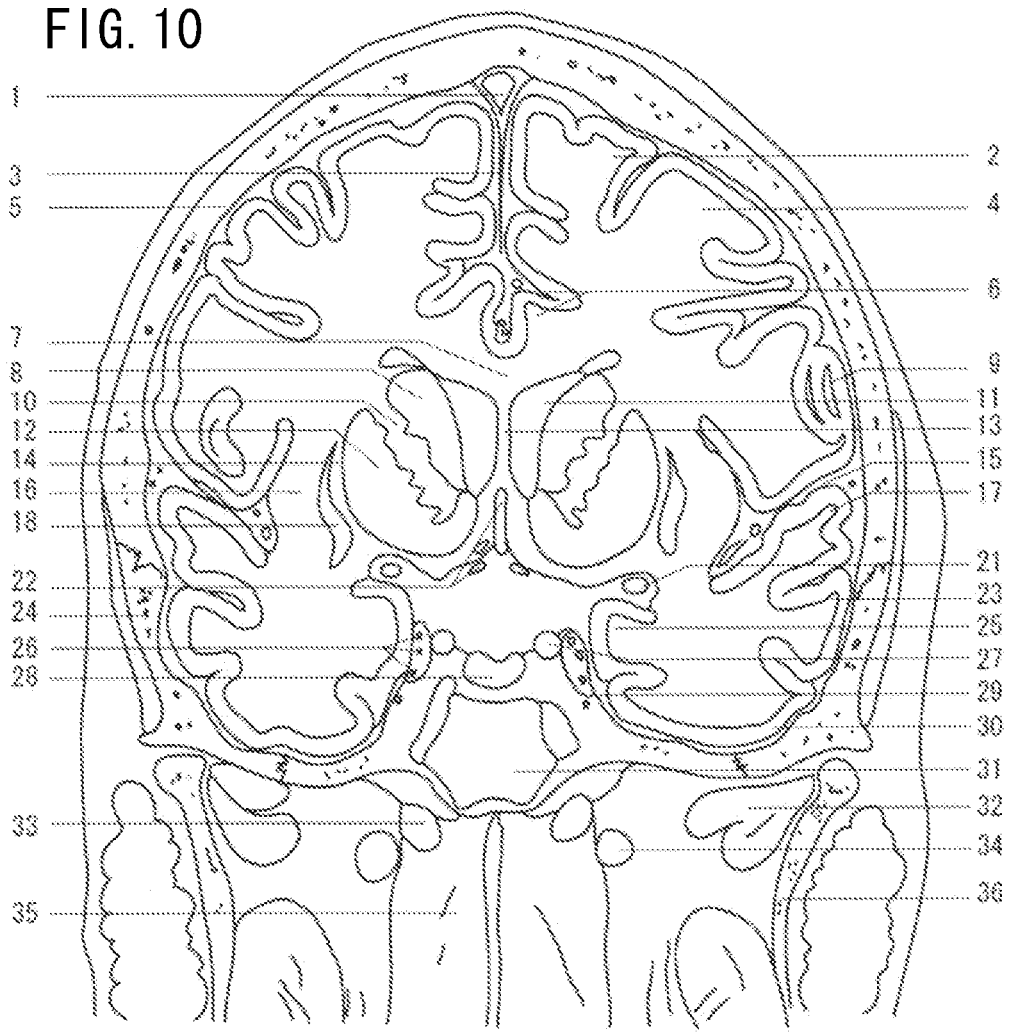

FIG. 10

1 superior sagittal sinus
2 superior frontal gyrus
3 falx cerebri
4 middle frontal gyrus
5 parietal bone
6 cingulate sulcus and gyrus
7 corpus callosum (trunk)
8 caudate nucleus (head)
9 inferior frontal gyrus
10 internal capsule (anterior limb)
11 lateral ventricle (anterior horn)
12 putamen
13 septum pellucidum
14 external capsule
15 lateral sulcus
16 capsula extrema
17 superior temporal gyrus
18 claustrum
21 middle cerebral artery
22 optic chiasm and anterior cerebral artery
23 middle temporal gyrus
24 temporal bone
25 parahippocampal gyrus
26 oculomotor, trochlear and abducens nerves (cranial nerves III, IV, VI)
27 internal carotid artery
28 pituitary gland
29 cavernous sinus
30 lateral occipitoremporal gyrus
31 sphenoid sinus
32 lateral pterygoid muscle
33 eustachian tube
34 levator veli palatini muscle
35 nasopharynx
36 mandible (ramus)

MEDICAL IMAGE DISPLAY APPARATUS, MEDICAL IMAGE DISPLAY METHOD AND PROGRAM

CROSS-REFERENCE TO RELATED APPLICATION

This application is based upon and claims the benefit of priority from Japanese Patent Application No. 2010-024587 filed on Feb. 5, 2010, of which the contents are incorporated herein by reference.

BACKGROUND OF THE INVENTION

1. Field of the Invention

The present invention relates to a medical image display apparatus, a medical image display method, and a program for displaying medical tomographic images.

2. Description of the Related Art

Heretofore, in the field of medical images, often it has been customary for a doctor to check names and regions of tissues that are included in displayed images when the doctor reads images for diagnosis. Usually, the doctor checks the images with an anatomy atlas. However, it is tedious and time-consuming to use an anatomy atlas, and further, an anatomy atlas does not have all of the sectional figures corresponding to arbitrary tomographic images. Therefore, an anatomy atlas may not have sectional figures that correspond to the tomographic images that the doctor reads for diagnosis.

Japanese Laid-Open Patent Publication No. 2008-073397 discloses an anatomical figure selecting method, an anatomical figure selecting apparatus, and a medical network system. Specifically, the anatomical figure selecting apparatus includes an image server recording therein a medical image database (DB), an anatomical figure database (DB), and an attribute information database (DB). When the image server receives a transfer request to transfer an anatomical figure, it reads a medical image, which agrees with a file name included in the transfer request from the medical image DB, and recognizes the body region that has been imaged. The anatomical figure selecting apparatus selects an anatomical figure of a body region recorded in the attribute information DB, which agrees with the recognized body region, as an anatomical figure that is most suitable for the medical image.

However, the disclosed anatomical figure selecting apparatus fails to display an anatomical image corresponding to an arbitrary tomographic image that the doctor reads for diagnosis.

SUMMARY OF THE INVENTION

An object of the present invention is to provide a medical image display apparatus, a medical image display method, and a program for displaying an anatomical figure, which is close to a tomographic image that a doctor reads for diagnosis.

To achieve the above objects, there is provided in accordance with the present invention a medical image display apparatus comprising an image database for recording therein a three-dimensional standard image of a model subject, a three-dimensional anatomical image corresponding to the three-dimensional standard image, and anatomical information representative of names of living tissues, an image acquirer for acquiring a three-dimensional medical image of an examinee, a medical tomographic image identifier for identifying a medical tomographic image in the three-dimensional medical image based on a user's instruction, a standard tomographic image identifier for identifying a standard tomographic image in the three-dimensional standard image, which corresponds to the medical tomographic image, an anatomical tomographic image identifier for identifying an anatomical tomographic image in the three-dimensional anatomical image, which corresponds to the standard tomographic image, and a display controller for displaying the medical tomographic image and the anatomical tomographic image on a display unit, while also displaying the names of living tissues over the anatomical tomographic image based on the anatomical information.

The image database records therein a plurality of three-dimensional standard images of model subjects, a plurality of three-dimensional anatomical images corresponding to the three-dimensional standard images, and anatomical information representative of names of living tissues. The standard tomographic image identifier identifies a standard tomographic image, which corresponds to the medical tomographic image, from the three-dimensional standard image of the model subject that corresponds to the examinee, and the anatomical tomographic image identifier identifies an anatomical tomographic image, which corresponds to the identified standard tomographic image, from the three-dimensional anatomical image that corresponds to the examinee.

The standard tomographic image identifier may perform a positioning process to identify the standard tomographic image, which is in conformity with the medical tomographic image at a level higher than a predetermined value.

The medical image display apparatus may further comprise a body surface extractor for extracting a body surface of the examinee from the three-dimensional medical image, and an image corrector for correcting the medical tomographic image based on misalignment between the extracted body surface of the examinee and a body surface of the model subject, wherein the standard tomographic image identifier identifies the standard tomographic image in the three-dimensional standard image, which corresponds to the medical tomographic image that is corrected by the image corrector, and the display controller displays, on the display unit, the medical tomographic image identified by the medical tomographic image identifier and which is not corrected by the image corrector, and the anatomical tomographic image.

To achieve the above object, there is also provided in accordance with the present invention a medical image display method of displaying images with a computer including an image database for recording therein a three-dimensional standard image of a model subject, a three-dimensional anatomical image corresponding to the three-dimensional standard image, and anatomical information representative of names of living tissues, comprising the steps of acquiring a three-dimensional medical image of an examinee, identifying a medical tomographic image in the three-dimensional medical image based on a user's instruction, identifying a standard tomographic image in the three-dimensional standard image, which corresponds to the medical tomographic image, identifying an anatomical tomographic image in the three-dimensional anatomical image, which corresponds to the standard tomographic image, and displaying the medical tomographic image and the anatomical tomographic image on a display unit, while also displaying the names of living tissues over the anatomical tomographic image based on the anatomical information.

To achieve the above object, there is also provided in accordance with the present invention a program for enabling a computer, including an image database for recording therein a three-dimensional standard image of a model subject, a three-dimensional anatomical image corresponding to the three-dimensional standard image, and anatomical information representative of names of living tissues, to function as image acquiring means for acquiring a three-dimensional medical image of an examinee, medical tomographic image identifying means for identifying a medical tomographic image in the three-dimensional medical image based on a user's instruction, standard tomographic image identifying means for identifying a standard tomographic image in the three-dimensional standard image, which corresponds to the medical tomographic image, anatomical tomographic image identifying means for identifying an anatomical tomographic image in the three-dimensional anatomical image, which corresponds to the standard tomographic image, and display controlling means for displaying the medical tomographic image and the anatomical tomographic image on a display unit, while also displaying the names of living tissues over the anatomical tomographic image based on the anatomical information.

According to the present invention, based on a user's instruction, a medical tomographic image in a three-dimensional medical image of an examinee is identified, a standard tomographic image in a three-dimensional standard image, which corresponds to the identified medical tomographic image, is identified, and an anatomical tomographic image in a three-dimensional anatomical image, which corresponds to the identified standard tomographic image, is identified. The medical tomographic image and the anatomical tomographic image are displayed on the display unit, and names of living tissues are displayed over the anatomical tomographic image based on anatomical information. Therefore, an anatomical figure, which is close to the medical tomographic image of the examinee that is read for diagnosis, is displayed on the display unit.

The image data base records therein a plurality of three-dimensional standard images of model subjects, a plurality of three-dimensional anatomical images corresponding to the three-dimensional standard images, and anatomical information representative of names of living tissues. The standard tomographic image identifier identifies a standard tomographic image, which corresponds to the medical tomographic image, from the three-dimensional standard image of the model subject that corresponds to the examinee, and the anatomical tomographic image identifier identifies an anatomical tomographic image in the three-dimensional anatomical image, which corresponds to the identified standard tomographic image. Therefore, an anatomical figure, which is close to the medical tomographic image of the examinee that is read for diagnosis, is displayed on the display unit.

The body surface of the examinee is extracted from the three-dimensional medical image, and the medical tomographic image is corrected based on a misalignment between the extracted body surface and the body surface of the model subject. A standard tomographic image corresponding to the corrected medical tomographic image is identified, and then an anatomical tomographic image is identified. Consequently, even if the body surface of the model subject and the body surface of the examinee are not in alignment with each other, an anatomical tomographic image, which is close to the medical tomographic image that is read for diagnosis, can accurately be identified, and an anatomical figure, which is close to the medical tomographic image, can be displayed.

The above and other objects, features, and advantages of the present invention will become more apparent from the following description when taken in conjunction with the accompanying drawings in which preferred embodiments of the present invention are shown by way of illustrative example.

BRIEF DESCRIPTION OF THE DRAWINGS

FIG. 5 is a diagram showing by way of example an anatomical tomographic image and names of living tissues, which are displayed according to the first embodiment;

FIG. 10 is a diagram showing by way of example an anatomical tomographic image and names of living tissues, which are displayed according to the second embodiment.

DESCRIPTION OF THE PREFERRED EMBODIMENTS

Medical image display methods according to preferred embodiments of the present invention in relation to a medical image display apparatus, and programs for carrying out the medical image display methods will be described in detail below with reference to the accompanying drawings.

First Embodiment

Figure 1:
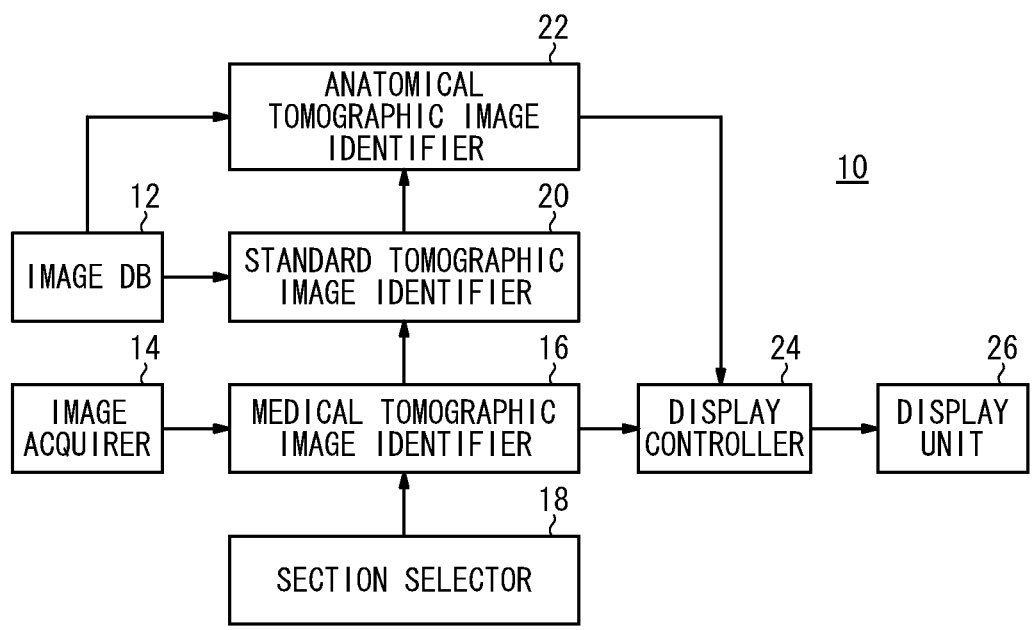
FIG. 1 is an electric block diagram of a medical image display apparatus according to a first embodiment of the present invention.

FIG. 1 is an electric block diagram of a medical image display apparatus 10 according to a first embodiment of the present invention. As shown in FIG. 1, the medical image display apparatus 10 comprises an image database (DB) 12, an image acquirer 14, a medical tomographic image identifier 16, a section selector 18, a standard tomographic image identifier 20, an anatomical tomographic image identifier 22, a display controller 24, and a display unit 26. When an information processor (computer) reads and executes a certain program, the information processor functions as the aforementioned image acquirer 14, the medical tomographic image identifier 16, the standard tomographic image identifier 20, the anatomical tomographic image identifier 22, and the display controller 24.

The image database 12 records therein a three-dimensional standard image of a model subject, a three-dimensional anatomical image corresponding to the three-dimensional standard image, and anatomical information representative of names of living tissues. The three-dimensional standard image is a three-dimensional image of the model subject, which is generated by a medical image capturing apparatus such as an X-ray CT apparatus, an MRI apparatus, or the like. The three-dimensional image comprises a plurality of axial tomographic images. The image database 12 records therein a plurality of three-dimensional standard images of model subjects, which may be classified according to gender and age. Alternatively, the image database 12 may record therein a plurality of three-dimensional standard images of model subjects, classified according to other factors such as height, weight, etc.

The three-dimensional anatomical image is a three-dimensional anatomical image, which corresponds to the recorded three-dimensional standard image, i.e., an anatomical image of the model subject represented by the three-dimensional standard image. The three-dimensional anatomical image comprises images of anatomical figures corresponding to respective axial tomographic images of the three-dimensional standard image. Since the image database 12 records therein a plurality of three-dimensional standard images, the image database 12 also records therein a plurality of three-dimensional anatomical images, which correspond to the three-dimensional standard image. The anatomical information represents names of living tissues of the model subject. The image database 12 records therein anatomical information representing names of living tissue regions, which are indicated by the three-dimensional anatomical images.

The image acquirer 14 acquires a three-dimensional medical image of a subject examinee, which is captured by a medical image capturing apparatus. More specifically, the image acquirer 14 acquires a three-dimensional medical image from an external apparatus. The three-dimensional medical image comprises a plurality of axial tomographic images. The external apparatus may be a medical image capturing apparatus, or a recording medium, which records therein a three-dimensional medical image. The image acquirer 14 also acquires examinee information representative of the gender, age, weight, height, etc., of the examinee, which has been recorded in association with the acquired three-dimensional medical image. The three-dimensional medical image acquired by the image acquirer 14 and the three-dimensional standard image recorded in the image database 12 are captured by the same type of medical image capturing apparatus, e.g., an X-ray CT apparatus. The image acquirer 14 outputs the acquired three-dimensional medical image and the acquired examinee information to the medical tomographic image identifier 16.

The medical tomographic image identifier 16 identifies a tomographic image (hereinafter referred to as a "medical tomographic image") in the three-dimensional medical image acquired by the image acquirer 14, depending on an instruction from a user of the medical image display apparatus 10. More specifically, the user operates the section selector 18, which may be a mouse or a keyboard, for example, in order to select a desired section, and the medical tomographic image identifier 16 identifies a medical tomographic image corresponding to the selected section from the three-dimensional medical image. At this time, the display controller 24 may display the three-dimensional medical image acquired by the image acquirer 14, thus enabling the user to select a desired section by operating the section selector 18, while simultaneously viewing the displayed three-dimensional medical image. Alternatively, a display apparatus (not shown) may display the three-dimensional medical image acquired by the image acquirer 14. The medical tomographic image identifier 16 outputs the identified medical tomographic image to the standard tomographic image identifier 20 and the display controller 24, and also outputs the acquired examinee information to the standard tomographic image identifier 20.

The standard tomographic image identifier 20 acquires the examinee information (gender, age, etc.), which was acquired by the image acquirer 14 from the medical tomographic image identifier 16, and also acquires from the image database 12 a three-dimensional standard image corresponding to the acquired examinee information. The standard tomographic image identifier 20 identifies a tomographic image (hereinafter referred to as a "standard tomographic image") in the three-dimensional standard image, which corresponds to the medical tomographic image identified by the medical tomographic image identifier 16. In other words, the standard tomographic image identifier 20 identifies from the standard tomographic image a standard tomographic image corresponding to the section of the three-dimensional medical image selected by the user. The standard tomographic image identifier 20 outputs positional information of the identified standard tomographic image to the anatomical tomographic image identifier 22.

More specifically, the standard tomographic image identifier 20 performs a positioning process in order to identify a standard tomographic image, which is in conformity with the medical tomographic image at a level higher than a predetermined value. In the present embodiment, the standard tomographic image identifier 20 identifies a standard tomographic image, which is in conformity with the medical tomographic image at a level higher than a predetermined value, and which is in closest conformity with the medical tomographic image. Alternatively, the standard tomographic image identifier 20 may identify a standard tomographic image, which is in closest conformity with the medical tomographic image, regardless of whether or not the standard tomographic image is in conformity with the medical tomographic image at a level higher than a predetermined value. The positioning process may be the process disclosed in Japanese Laid-Open Patent Publication No. 2008-043524.

The process disclosed in Japanese Laid-Open Patent Publication No. 2008-043524 will briefly be described below. According to the disclosed process, first, standard coordinate positions of slice images of a standard tomographic image, and standard feature quantities of the slice images are recorded. The standard feature quantities include, for example, a feature quantity representative of a roundness of the entire body of the examinee, an air region feature quantity representative of the proportion of an air region of the examinee, a bone region feature quantity representative of the proportion of a bone region of the examinee, and a soft tissue feature quantity representative of the proportion of a soft tissue of the examinee. The positioning process is carried out by determining feature quantities of a captured tomographic image, searching for recorded feature quantities, which are in closest conformity with the determined feature quantities, and recording coordinate positions corresponding to the searched-for recorded feature quantities as coordinate positions of the captured tomographic image.

When a standard tomographic image is identified, the anatomical tomographic image identifier 22 identifies an anatomical tomographic image in a three-dimensional anatomical image, which corresponds to the standard tomographic image. More specifically, the anatomical tomographic image identifier 22 identifies an anatomical tomographic image of a section, which corresponds to the section selected by the user, of the three-dimensional medical image from a three-dimensional anatomical image. The anatomical tomographic image identifier 22 reads the identified anatomical tomographic image from the image database 12, and outputs the read anatomical tomographic image to the display controller 24. At this time, the anatomical tomographic image identifier 22 also reads corresponding anatomical information from the image database 12, and outputs the read anatomical information to the display controller 24.

The display controller 24 displays the medical tomographic image and the anatomical tomographic image on the display unit 26, while also displaying names of living tissues over the anatomical tomographic image based on the anatomical information.

Figure 2:
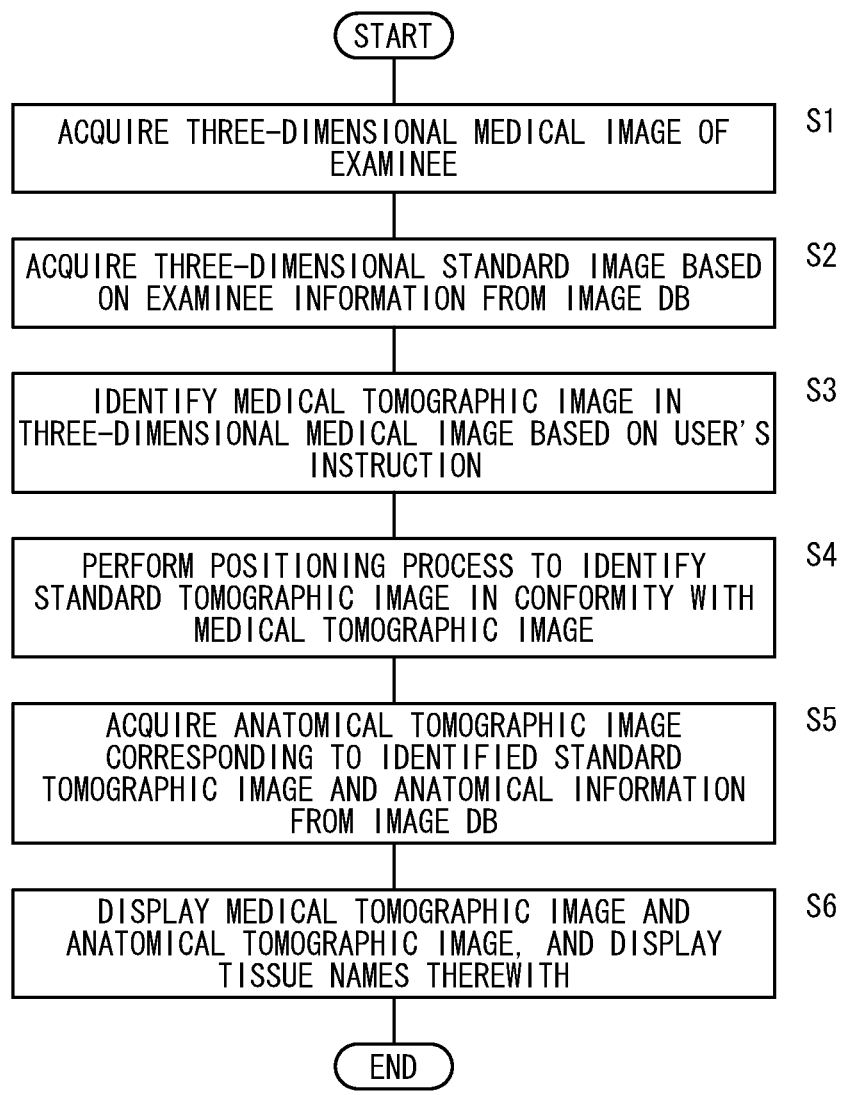
FIG. 2 is a flowchart of an operation sequence of the medical image display apparatus according to the first embodiment.

An operation sequence carried out by the medical image display apparatus 10 according to the first embodiment will be described below with reference to the flowchart shown in FIG. 2.

In step S1, the image acquirer 14 acquires a three-dimensional medical image of an examinee, which is captured by a medical image capturing apparatus. At this time, the image acquirer 14 also acquires examinee information associated with the three-dimensional medical image.

Figure 3:
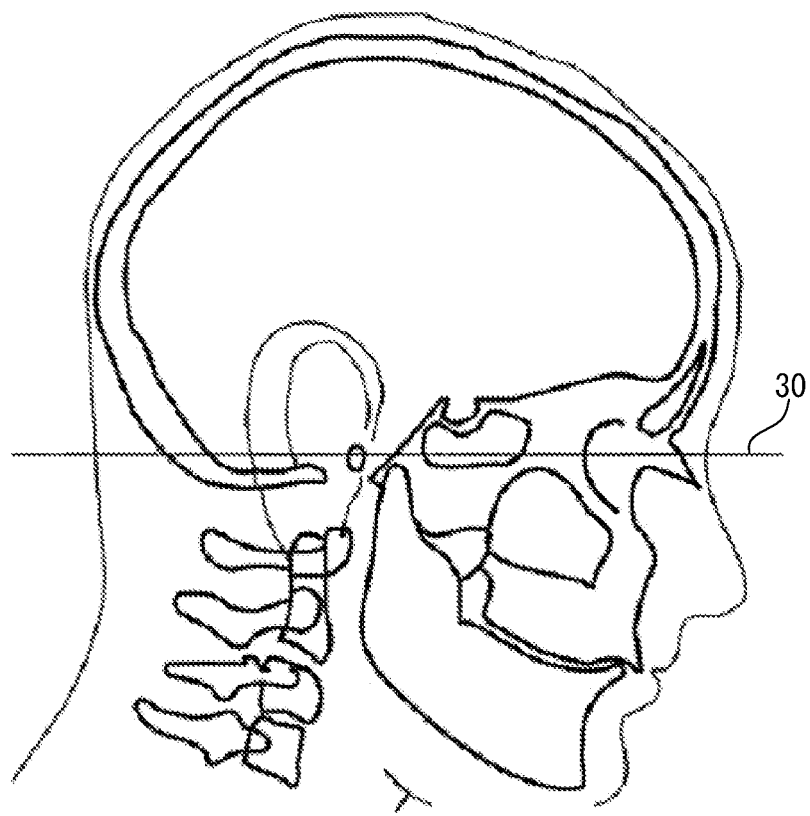
FIG. 3 is a diagram showing an example of a section selected by a user according to the first embodiment.

Then, in step S2, the standard tomographic image identifier 20 acquires a three-dimensional standard image from the image database 12 corresponding to the examinee information. Next, in step S3, the medical tomographic image identifier 16 identifies, from the three-dimensional medical image acquired in step S1, a medical tomographic image of a section, which is selected by the user operating the section selector 18. FIG. 3 shows by way of example a section 30 selected by the user. For purposes of explanation, it shall be assumed that the section selected in step S3 is an axial section.

Figure 4:
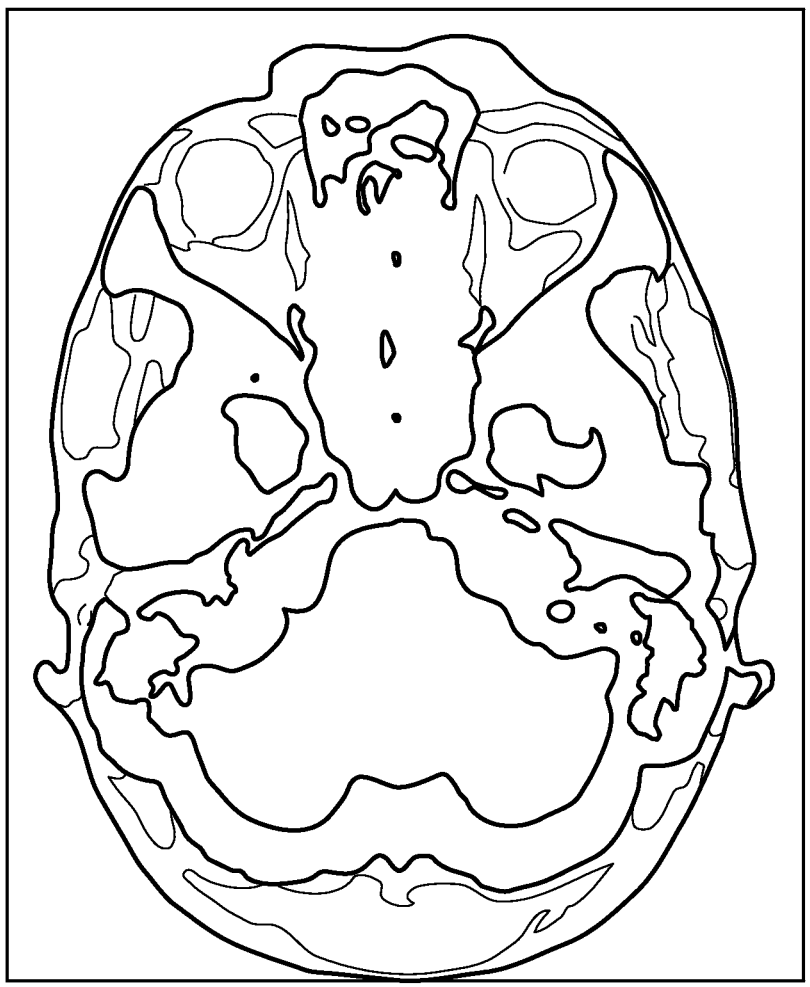
FIG. 4 is a diagram showing an example of a specified standard tomographic image according to the first embodiment.

Then, in step S4, the standard tomographic image identifier 20 identifies, from the three-dimensional standard image acquired in step S2, a standard tomographic image corresponding to the medical tomographic image selected in step S3. At this time, the standard tomographic image identifier 20 identifies a standard tomographic image, which is in conformity with the medical tomographic image at a level higher than a predetermined value, and which is in closest conformity with the medical tomographic image, according to the above-described positioning process. The location (position) of the section in the three-dimensional standard image is recognized, which corresponds to the section that has been selected by the user in the three-dimensional medical image. FIG. 4 shows an example of the identified standard tomographic image.

If the section selected by the user is an axial section, then the standard tomographic image identifier 20 may determine the distance by which the selected medical tomographic image is spaced from the top of the head of the examinee, and may further identify the image of a section that is spaced by the distance from the top of the head of the model subject as a standard tomographic image. Since the examinee, the three-dimensional medical image of whom has been captured, and the model subject, the three-dimensional standard image of which is recorded in the image database 12, are of the same gender, age, height, etc., the medical tomographic image and the standard tomographic image define tomographic images, which are at substantially the same position.

Then, in step S5, the anatomical tomographic image identifier 22 identifies from the three-dimensional anatomical image an anatomical tomographic image, which corresponds to the identified standard tomographic image, and acquires the identified anatomical tomographic image and corresponding anatomical information from the image database 12. Since the three-dimensional anatomical image is a three-dimensional image indicative of an anatomical figure of the model subject represented by the three-dimensional standard image, if the position of the standard tomographic image is known, then the section in the three-dimensional anatomical image can be recognized, thus making it possible to identify the anatomical tomographic image.

Then, the display controller 24 displays the medical tomographic image identified in step S3 and the anatomical tomographic image acquired in step S5 on the display unit 26, while also displaying names of living tissues included in the anatomical tomographic image over the displayed anatomical tomographic image in step S6.

FIG. 5 shows by way of example an anatomical tomographic image and the names of living tissues, which are displayed on the display unit 26. The anatomical tomographic image shown in FIG. 5 represents an anatomical figure corresponding to the standard tomographic image shown in FIG. 4, and is associated with the names of living tissues included in the anatomical figure. The display unit 26 displays an anatomical figure, which is close to the section of the medical tomographic image that is read by the user for diagnosis, and the names of living tissues included in the anatomical figure. Therefore, the user can easily observe the anatomical figure, which is close to the section of the medical tomographic image that the user reads for diagnosis.

According to the first embodiment, as described above, a medical tomographic image in a captured three-dimensional medical image of an examinee is identified according to an instruction from the user, and a standard tomographic image in a three-dimensional standard image, which corresponds to the identified medical tomographic image, is identified. Then, an anatomical tomographic image in a three-dimensional anatomical image, which corresponds to the identified standard tomographic image, is identified. The medical tomographic image and the anatomical tomographic image are displayed on the display unit 26, and based on anatomical information, the names of living tissues are displayed together therewith over the displayed anatomical tomographic image. Consequently, the display unit 26 displays an anatomical figure, which is close to the selected medical tomographic image, together with the names of living tissues included in the anatomical figure.

Second Embodiment

Figure 6:
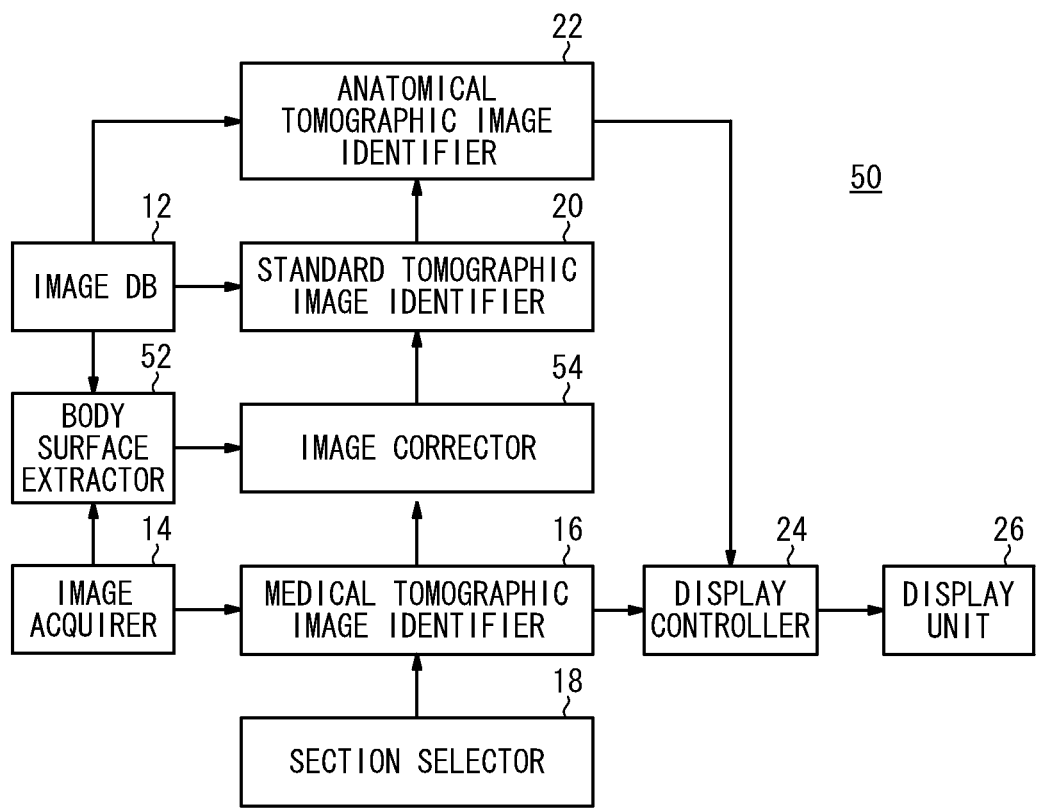
FIG. 6 is an electric block diagram of a medical image display apparatus according to a second embodiment of the present invention.

FIG. 6 is an electric block diagram of a medical image display apparatus 50 according to a second embodiment of the present invention. As shown in FIG. 6, the medical image display apparatus 50 comprises an image database 12, an image acquirer 14, a medical tomographic image identifier 16, a section selector 18, a standard tomographic image identifier 20, an anatomical tomographic image identifier 22, a display controller 24, a display unit 26, a body surface extractor 52, and an image corrector 54. Components of the medical image display apparatus 50, which are identical or equivalent to those of the medical image display apparatus 10 shown in FIG. 1, are denoted by identical reference characters, and such features will not be described in detail below. The image database 12 records therein information representative of a body surface of a model subject, which is represented by a three-dimensional standard image (the region of a model subject in a three-dimensional standard image).

The body surface extractor 52 acquires, from the image database 12, information representative of the body surface of the model subject, the three-dimensional standard image of which is acquired from the image database 12 by the standard tomographic image identifier 20, and outputs the acquired information to the image corrector 54. The body surface extractor 52 also extracts the body surface of the examinee (examinee region) from the three-dimensional image acquired by the image acquirer 14, and outputs the extracted body surface to the image corrector 54. The body surface extractor 52 can extract a body surface by extracting a high-density region as a subject region, which has an image density higher than a reference density. Alternatively, the body surface extractor 52 can extract a body surface by extracting high-density regions having an image density higher than a reference density, performing a smoothing process on the extracted high-density regions using a median filter, and extracting a subject region based on an area of each of the high-density regions. Further, alternatively, the body surface extractor 52 can extract a body surface according to the process disclosed in Japanese Laid-Open Patent Publication No. 2009-082463. According to the process disclosed in Japanese Laid-Open Patent Publication No. 2009-082463, a body surface is extracted through binarization of each of a plurality of tomographic images based on a certain image density that serves as a reference value, and by classifying images included in the binarized tomographic images into a first image group, made up of images within the examinee, and a second image group, made up of images outside the examinee, based on a positional relationship between each of the images and other images within the same tomographic images, and a positional relationship between each of the images and other images within other tomographic images.

The image corrector 54 corrects the medical tomographic image identified by the medical tomographic image identifier 16, based on a misalignment between the body surface of the model subject, which is represented by the three-dimensional standard image acquired by the body surface extractor 52, and the body surface of the examinee, which is represented by the three-dimensional medical image extracted by the body surface extractor 52. Such a misalignment serves as a basis for correcting the body surface of the examinee represented by the three-dimensional medical image, such that the body surface of the examinee represented by the three-dimensional medical image overlaps (i.e., becomes aligned with) the body surface of the model subject represented by the three-dimensional standard image. The image corrector 54 corrects the medical tomographic image based on the misalignment.

Even though a three-dimensional standard image of the model subject is used, the gender, age, etc., of which are the same as those of the examinee, the three-dimensional medical image and the three-dimensional standard image may be misaligned from each other due to individual differences, or due to the examinee's posture at a time when the examinee is imaged, thus tending to lower the accuracy with which the standard tomographic image in the three-dimensional standard image is identified so as to be close to the identified three-dimensional medical image. Therefore, as described above, the image corrector 54 corrects the three-dimensional medical image in order to eliminate such misalignment. The image corrector 54 outputs the corrected three-dimensional medical image to the standard tomographic image identifier 20.

The standard tomographic image identifier 20 identifies a standard tomographic image in the three-dimensional standard image, which corresponds to the medical tomographic image corrected by the image corrector 54.

Figure 7:
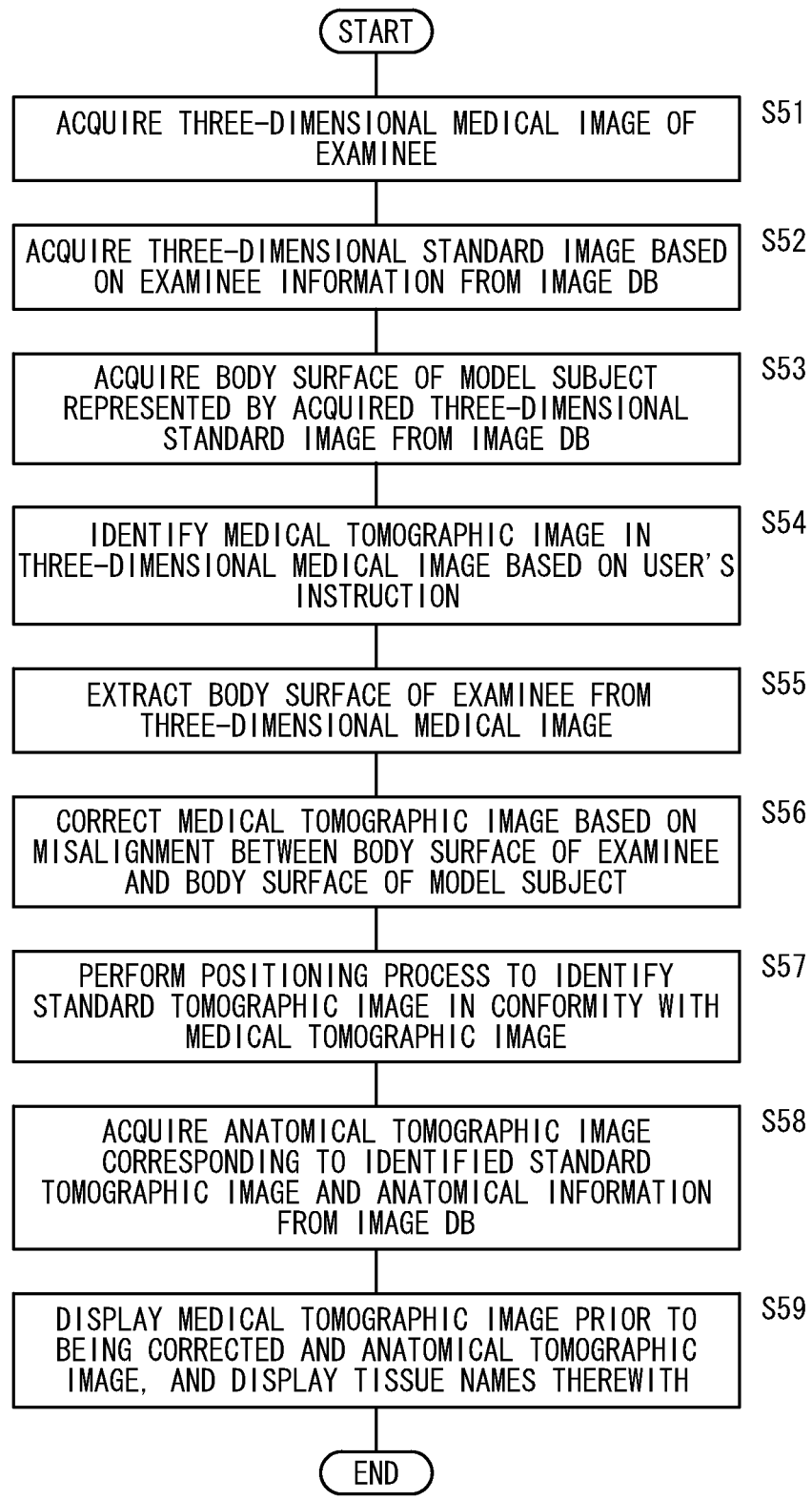
FIG. 7 is a flowchart of an operation sequence of the medical image display apparatus according to the second embodiment.

An operation sequence carried out by the medical image display apparatus 50 according to the second embodiment will be described below with reference to the flowchart shown in FIG. 7.

In step S51, the image acquirer 14 acquires a three-dimensional medical image of an examinee, which is captured by a medical image capturing apparatus. At this time, the image acquirer 14 also acquires examinee information associated with the three-dimensional medical image.

Then, in step S52, the standard tomographic image identifier 20 acquires a three-dimensional standard image from the image database 12 that corresponds to the examinee information. Next, in step S53, the body surface extractor 52 extracts the body surface of the model subject, the three-dimensional standard image of which has been acquired from the image database 12 in step S52.

Figure 8:
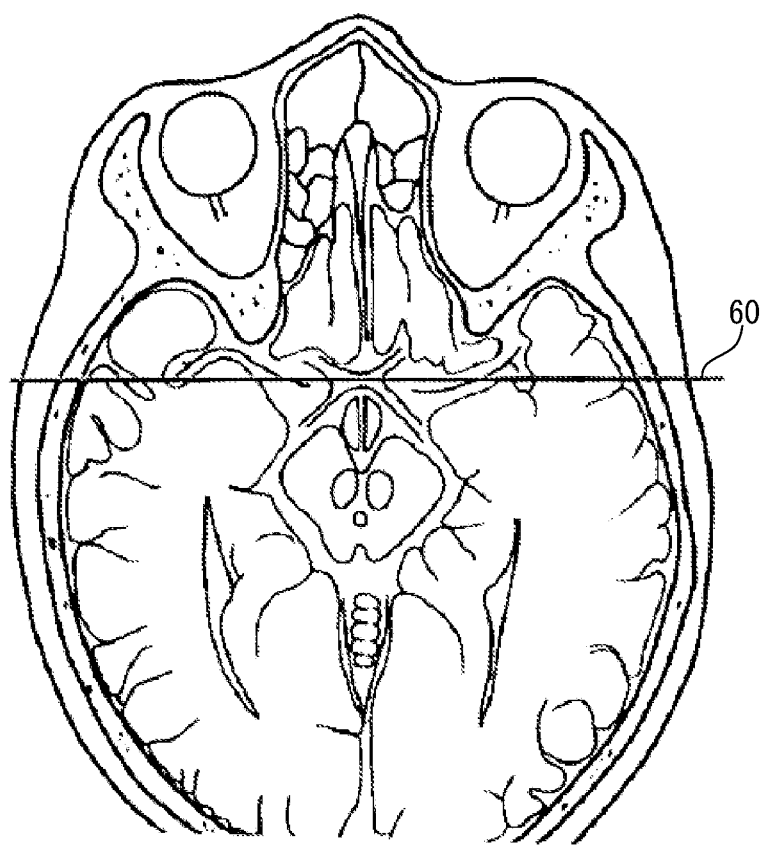
FIG. 8 is a diagram showing an example of a section selected by a user according to the second embodiment.

In step S54, the medical tomographic image identifier 16 identifies, from the three-dimensional medical image acquired in step S51, a medical tomographic image of a section that is selected by the user operating the section selector 18. FIG. 8 shows, by way of example, a section 60 selected by the user. For descriptive purposes, it shall be assumed that the section selected in step S3 is a coronal section.

Then, in step S55, the body surface extractor 52 extracts the body surface of the examinee from the three-dimensional medical image acquired in step S51. In step S56, the image corrector 54 corrects the medical tomographic image identified in step S54, based on a misalignment between the body surface of the model subject acquired in step S53 and the body surface of the examinee extracted in step S55. In this manner, a tomographic image of the section selected by the user is obtained when the three-dimensional medical image is corrected, such that the body surface of the examinee represented by the three-dimensional medical image is aligned with the body surface of the model subject represented by the three-dimensional standard image.

Figure 9:
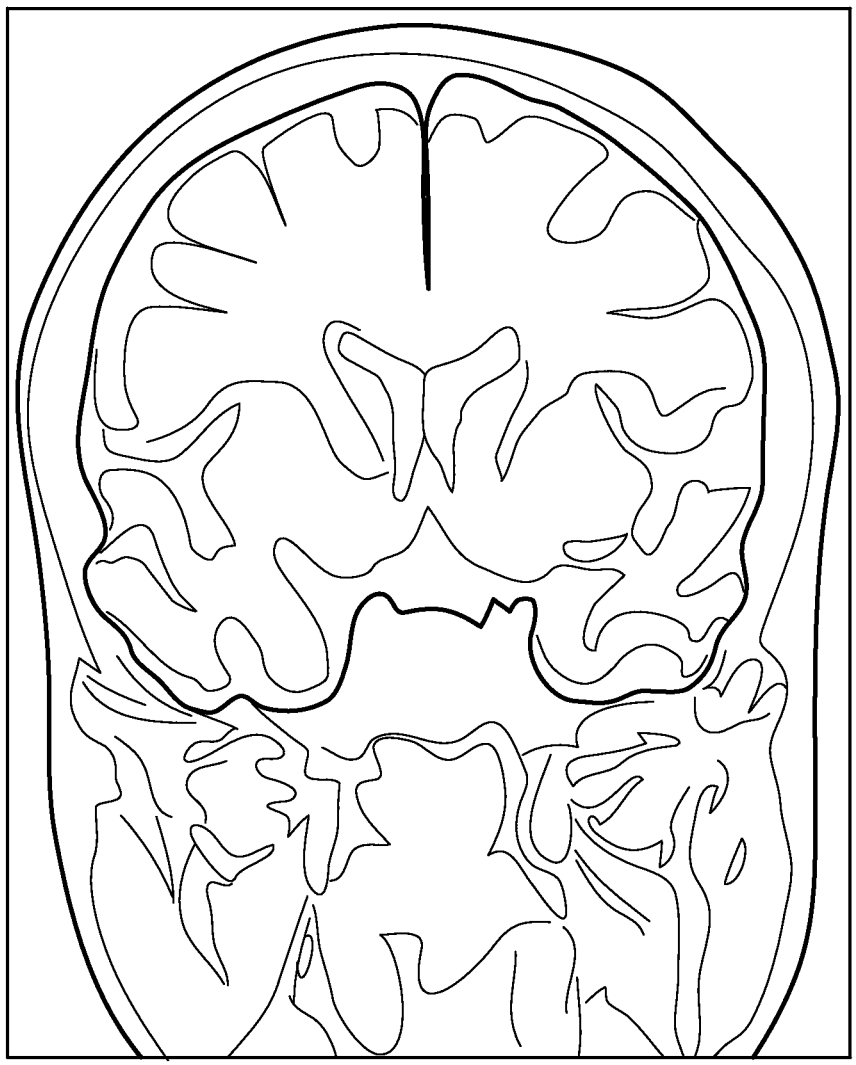
FIG. 9 is a diagram showing an example of a specified standard tomographic image according to the second embodiment.

Then, in step S57, the standard tomographic image identifier 20 identifies from the three-dimensional standard image acquired in step S52 a standard tomographic image corresponding to the medical tomographic image corrected in step S56. At this time, the standard tomographic image identifier 20 identifies a standard tomographic image, which is in conformity with the medical tomographic image at a level higher than a predetermined value, and which is in closest conformity with the medical tomographic image, according to the positioning process referred to above. The location (position) of the section within the three-dimensional standard image, which corresponds to the section that has been selected by the user in the three-dimensional medical image, is recognized. FIG. 9 shows an example of the identified standard tomographic image.

Then, in step S58, the anatomical tomographic image identifier 22 identifies an anatomical tomographic image, which corresponds to the identified standard tomographic image, from the three-dimensional anatomical image, and acquires the identified anatomical tomographic image and corresponding anatomical information from the image database 12. Since the three-dimensional anatomical image is a three-dimensional image indicative of an anatomical figure of the model subject, which is represented by the three-dimensional standard image, if the position of the standard tomographic image is known, then the section in the three-dimensional anatomical image is recognized.

Then, in step S59, the display controller 24 displays on the display unit 26 the medical tomographic image identified in step S54 (the medical tomographic image prior to being corrected in step S56), and the anatomical tomographic image acquired in step S58, and also displays the names of living tissues included in the anatomical tomographic image over the displayed anatomical tomographic image.

FIG. 10 shows by way of example the anatomical tomographic image together with the names of living tissues that are displayed on the display unit 26. The anatomical tomographic image shown in FIG. 10 represents an anatomical figure, which corresponds to the standard tomographic image shown in FIG. 9, and which is associated with names of living tissues included in the anatomical figure. The display unit 26 displays an anatomical figure, which is close to the section of the medical tomographic image that is read by the user for diagnosis, together with the names of living tissues included in the anatomical figure. Therefore, the user can easily see the anatomical figure, which is close to the section of the medical tomographic image that the user reads for diagnosis.

According to the second embodiment, as described above, the body surface of an examinee is extracted, and a medical tomographic image is corrected based on misalignment between the extracted body surface of the examinee and the body surface of a model subject. A standard tomographic image corresponding to the corrected medical tomographic image is identified, and then an anatomical tomographic image is identified. Therefore, even if the body surface of the model subject and the body surface of the examinee are not in alignment with each other, an anatomical tomographic image, which is close to the medical tomographic image that the user reads for diagnosis, can accurately be identified, and the display unit 26 displays an anatomical figure that is close to the medical tomographic image.

The above embodiments of the present invention may be modified as follows:

(1) In the first and second embodiments, the image acquirer 14 acquires a three-dimensional medical image of an examinee, which is associated with examinee information, and the standard tomographic image identifier 20 acquires the associated examinee information. However, the user may operate an operation unit (not shown) in order to enter examinee information, and the standard tomographic image identifier 20 may acquire the entered examinee information.

(2) In the second embodiment, a three-dimensional standard image and the body surface of the model subject, which is represented by the three-dimensional standard image, are recorded in the image database 12. However, the body surface need not be recorded in the image database 12. Alternatively, the body surface extractor 52 may extract the body surface of the model subject, which is represented by the three-dimensional standard image recorded in the image database 12.

(3) In the first and second embodiments, the display unit 26 displays a medical tomographic image and an anatomical tomographic image. However, the display unit 26 may also display a standard tomographic image, which is identified by the standard tomographic image identifier 20.

(4) In the first embodiment, an axial section is selected, and in the second embodiment, a coronal section is selected. However, sections other than axial and coronal sections may be selected by the user by operating the section selector 18.

(5) A three-dimensional anatomical image is made up of a plurality of anatomical tomographic images of respective axial sections. However, the three-dimensional anatomical image may be made up of a plurality of anatomical tomographic images of respective sections other than axial sections. The three-dimensional anatomical image may be of a size identical to or different from the three-dimensional standard image. The three-dimensional anatomical image may be expressed as a three-dimensional surface, or as contour lines on sections. If contour lines are not recorded as image information, then an anatomical tomographic image for display may be generated using three-dimensional surface images of organs, contour lines of organs, etc. The three-dimensional anatomical image may be a collection of three-dimensional images of organs. In this case, an anatomical tomographic image of a section to be displayed may be generated from a three-dimensional image of such organs.

An anatomical tomographic image may represent an anatomical figure with names of living tissues assigned thereto. In this case, the image database 12 does not need to record therein anatomical information. Rather, the user can select only sections parallel to the anatomical tomographic image by operating the section selector 18. More specifically, for example, if a three-dimensional anatomical image is made up of a plurality of anatomical tomographic images of coronal sections, and the user selects an axial section, then an anatomical figure of the axial section can be displayed, however, the names of living tissues cannot be displayed in association therewith.

Although certain preferred embodiments of the present invention have been shown and described in detail, it should be understood that various changes and modifications may be made to the embodiments without departing from the scope of the invention as set forth in the appended claims.

What is claimed is:

1. A medical image display apparatus (10, 50) comprising:
an image database (12) for recording therein a three-dimensional standard image of a model subject, a three-dimensional anatomical image corresponding to the three-dimensional standard image, and anatomical information representative of names of living tissues;
an image acquirer (14) for acquiring a three-dimensional medical image of an examinee;
a medical tomographic image identifier (16) for identifying a medical tomographic image in the three-dimensional medical image based on a user's instruction;
a standard tomographic image identifier (20) for identifying a standard tomographic image in the three-dimensional standard image, which corresponds to the medical tomographic image;
an anatomical tomographic image identifier (22) for identifying an anatomical tomographic image in the three-dimensional anatomical image, which corresponds to the standard tomographic image; and
a display controller (24) for displaying the medical tomographic image and the anatomical tomographic image on a display unit (26), while also displaying the names of living tissues over the anatomical tomographic image based on the anatomical information.

2. The medical image display apparatus (10, 50) according to claim 1,
wherein the image database (12) records therein a plurality of three-dimensional standard images of model subjects, a plurality of three-dimensional anatomical images corresponding to the three-dimensional standard images, and the anatomical information representative of the names of living tissues;
the standard tomographic image identifier (20) identifies the standard tomographic image, which corresponds to the medical tomographic image, from the three-dimensional standard image of the model subject that corresponds to the examinee; and
the anatomical tomographic image identifier (22) identifies an anatomical tomographic image, which corresponds to the identified standard tomographic image, from the three-dimensional anatomical image that corresponds to the examinee.

3. The medical image display apparatus (10, 50) according to claim 1, wherein the standard tomographic image identifier (20) performs a positioning process to identify the standard tomographic image, which is in conformity with the medical tomographic image at a level higher than a predetermined value.

4. The medical image display apparatus (10, 50) according to claim 1, further comprising:
a body surface extractor (52) for extracting a body surface of the examinee from the three-dimensional medical image; and an image corrector (54) for correcting the medical tomographic image based on a misalignment between the extracted body surface of the examinee and a body surface of the model subject, wherein the standard tomographic image identifier (20) identifies the standard tomographic image in the three-dimensional standard image, which corresponds to the medical tomographic image that is corrected by the image corrector, and the display controller (24) displays, on the display unit (26), the medical tomographic image identified by the medical tomographic image identifier (16) and which is not corrected by the image corrector (54), and the anatomical tomographic image.

5. A medical image display method of displaying images with a computer including an image database (12) for recording therein a three-dimensional standard image of a model subject, a three-dimensional anatomical image corresponding to the three-dimensional standard image, and anatomical information representative of names of living tissues, comprising the steps of:

acquiring a three-dimensional medical image of an examinee;

identifying a medical tomographic image in the three-dimensional medical image based on a user's instruction;

identifying a standard tomographic image in the three-dimensional standard image, which corresponds to the medical tomographic image;

identifying an anatomical tomographic image in the three-dimensional anatomical image, which corresponds to the standard tomographic image; and displaying the medical tomographic image and the anatomical tomographic image on a display unit, while also displaying the names of living tissues over the anatomical tomographic image based on the anatomical information.

6. A non-transitory, computer-readable medium having recorded thereon a program sufficient to cause a computer, which incorporates an image database (12) for recording therein i) a three-dimensional standard image of a model subject, ii) a three-dimensional anatomical image corresponding to the three-dimensional standard image, and iii) anatomical information representative of names of living tissues, to function as:

image acquiring means (14) for acquiring a three-dimensional medical image of an examinee;

medical tomographic image identifying means (16) for identifying a medical tomographic image in the three-dimensional medical image based on a user's instruction;

standard tomographic image identifying means (20) for identifying a standard tomographic image in the three-dimensional standard image, which corresponds to the medical tomographic image;

anatomical tomographic image identifying means (22) for identifying an anatomical tomographic image in the three-dimensional anatomical image, which corresponds to the standard tomographic image; and display controlling means (24) for displaying the medical tomographic image and the anatomical tomographic image on a display unit (26), while also displaying the names of living tissues over the anatomical tomographic image based on the anatomical information.

* * * * *